(12) United States Patent
Woolard et al.

(10) Patent No.: US 9,877,480 B2
(45) Date of Patent: *Jan. 30, 2018

(54) (S)-ABSCISIC ACID DERIVATIVES FOR ENHANCED GRAPE COLORATION

(71) Applicant: Valent BioSciences Corporation, Libertyville, IL (US)

(72) Inventors: Derek D. Woolard, Zion, IL (US); Gary T. Wang, Libertyville, IL (US); Rick Hopkins, Fresno, CA (US); Daniel C. Leep, Lindenhurst, IL (US); Gregory D. Venburg, Deerfield, IL (US)

(73) Assignee: Valent Biosciences LLC, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,793

(22) Filed: May 19, 2016

(65) Prior Publication Data

US 2016/0338351 A1 Nov. 24, 2016

Related U.S. Application Data

(60) Provisional application No. 62/163,607, filed on May 19, 2015.

(51) Int. Cl.
*A01N 57/20* (2006.01)
*A01N 37/42* (2006.01)

(52) U.S. Cl.
CPC ............. *A01N 37/42* (2013.01); *A01N 57/20* (2013.01)

(58) Field of Classification Search
None
See application file for complete search history.

(56) References Cited

U.S. PATENT DOCUMENTS

| 6,004,905 | A | * | 12/1999 | Abrams | A01N 49/00 504/193 |
| 8,247,349 | B2 | * | 8/2012 | Liu | C05C 1/00 504/116.1 |
| 2009/0124503 | A1 | | 5/2009 | Venburg et al. | |
| 2014/0087949 | A1 | | 3/2014 | Frackenpohl et al. | |

FOREIGN PATENT DOCUMENTS

WO   WO1994/015467   7/1994

OTHER PUBLICATIONS

Ueno, K.; et al. "Differences between the structural requirements for ABA 8'-hydroxylase inhibition and for ABA activity" Bioorganic and Medicinal Chemistry, 2005, v. 13, 3359-3370.*
International Search Report and Written Opinion dated Aug. 23, 2016 in corresponding PCT Application No. PCT/US2016/033170.
International Preliminary Report on Patentability and Written Opinion of the International Searching Authority, dated Nov. 21, 2017 in PCT/US2016/033170.

* cited by examiner

*Primary Examiner* — Mina Haghighatian
*Assistant Examiner* — Erin Hirt
(74) *Attorney, Agent, or Firm* — Wood, Phillips, Katz, Clark & Mortimer

(57) ABSTRACT

The present invention is directed to the treatment of grapes with 3'-methyl-(S)-abscisic acid, 3'-propargyl-(S)-abscisic acid, and/or salts thereof in order to enhance the color of the grapes.

9 Claims, No Drawings

(S)-ABSCISIC ACID DERIVATIVES FOR ENHANCED GRAPE COLORATION

FIELD OF THE INVENTION

The present invention is directed to methods for enhancing grape coloration comprising applying (S)-abscisic acid derivatives to the plants.

BACKGROUND OF THE INVENTION

Coloration is an important characteristic of commercially grown grapes. Grapes with uniform and desirable color can command premium prices in the market. In addition, color development is an important indication of grape maturation and impacts the harvest time. It is desirable for grape clusters in a field to mature at the same time in order to eliminate harvesting immature fruit with the mature fruit. Thus, pre-harvest treatments of grapes that promote uniform and early development of grape color have significant commercial value.

Currently, there are two products commercially available for enhancing grape coloration. One of the products, Ethrel® (available from and a registered trademark of Bayer) contains ethephon. Ethephon (2-chloroethylphosphonic acid) is an ethylene precursor which is rapidly converted into ethylene in plants. While ethephon is effective at enhancing fruit coloration, it is also difficult to apply to the grapes, requires high application rates, and does not provide consistent results. In some areas, there is also concern about the safety of ethephon use.

The other commercially available product, ProTone® (available from and a registered trademark of Valent BioSciences Corporation) contains (S)-abscisic acid. (S)-abscisic acid is a plant growth regulator that promotes plant or fruit maturity and color development by directly augmenting anthocyanin synthesis. While (S)-abscisic acid ("S-ABA") is very effective at enhancing fruit coloration, relatively high concentrations must be used in order to achieve desired results.

Accordingly, there is a need for new methods for enhancing grape coloration in order to produce highly marketable grapes. The new methods should be cost-effective for the growers and produce consistent and reliable coloration results.

SUMMARY OF THE INVENTION

The present invention is directed to methods for enhancing red grape coloration comprising applying 3'-methyl-(S)-abscisic acid, 3'-propargyl-(S)-abscisic acid, and salts thereof to the plants.

DETAILED DESCRIPTION OF THE INVENTION

Recently, Applicant discovered new S-ABA derivatives (see U.S. Patent Application No. 62/022,037 and Ser. No. 14/593,597). Applicant determined that two derivatives were unexpectedly more potent than S-ABA. Specifically, these derivatives are (2Z,4E)-5-((S)-1-hydroxy-2,3,6,6-tetramethyl-4-oxocyclohex-2-en-1-yl)-3-methylpenta-2,4-dienoic acid ("3'-methyl-(S)-abscisic acid") and (2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid ("3'-propargyl-(S)-abscisic acid"). The structures of these derivatives are below:

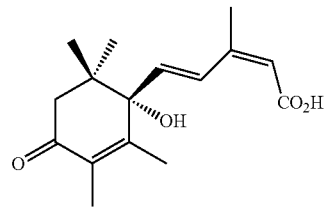

3'-methyl-(S)-abscisic acid

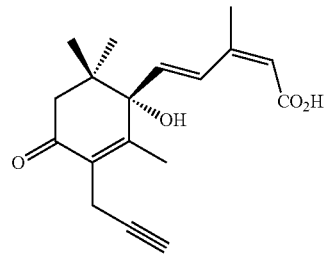

3'-propargyl-(S)-abscisic acid

Applicant unexpectedly found that the abscisic acid derivative 3'-methyl-(S)-abscisic acid provided excellent enhancement of grape coloration. Specifically, Applicant found that 3'-methyl-(S)-abscisic acid was ten times as effective as S-ABA for enhancing grape coloration. Further, Applicant unexpectedly discovered that a much lower rate of 3'-methyl-(S)-ABA was required to develop marketable coloration in comparison to S-ABA. For example, treatment of Crimson Seedless grapes with 0.6 to 0.8 mg per cluster (40 ppm, 15 to 20 mL) of 3'-methyl-(S)-ABA provided a similar coloration effect as treatment with 6 to 8 mg per cluster (400 ppm, 15 to 20 mL) of S-ABA. Additionally, Applicant unexpectedly discovered that 3'-methyl-(S)-ABA conferred coloration much faster than S-ABA at the same use rate. For example, treating of Crimson seedless grapes at 6 to 8 mg per cluster rate (400 ppm, 15 to 20 mL) with 3'-methyl-(S)-ABA provided ~90% marketable coloration in just two weeks, whereas it took five weeks for grapes treated with the same dose of S-ABA treated to reach the same level of coloration.

In an embodiment, the present invention is directed to methods for enhancing red grape coloration comprising applying an abscisic acid derivative selected from the group consisting of 3'-methyl-(S)-abscisic acid, 3'-propargyl-(S)-abscisic acid, and salts thereof to the plant.

In a preferred embodiment, the abscisic acid derivative applied to the plant is 3'-methyl-(S)-abscisic acid.

In another embodiment, the 3'-methyl-(S)-abscisic acid potassium salt is applied to the vine at a rate of from about 0.1 to about 10 mg per cluster. In a preferred embodiment, the 3'-methyl-(S)-abscisic acid is applied to the vine at a rate of from about 0.2 to about 8 mg per cluster. In a more preferred embodiment, the 3'-methyl-(S)-abscisic acid is applied to the vine at a rate of from about 0.3 to about 8 mg per cluster.

In a further embodiment, the 3'-methyl-(S)-abscisic acid is applied to the vine during the period beginning when the fruit is about 3 weeks before veraison and ending when the fruit is about 4 weeks after the onset of veraison. In a preferred embodiment, the 3'-methyl-(S)-abscisic acid is applied to the plant during the period beginning when the fruit is about 2 weeks before veraison and ending when the fruit is about 4 weeks after the onset of veraison. In a more preferred embodiment, the 3'-methyl-(S)-abscisic acid is applied to the plant during the period beginning when the fruit is about 1 week before veraison and ending when the fruit is about 4 weeks after the onset of veraison. In a most preferred embodiment, the 3'-methyl-(S)-abscisic acid is applied to the plant during the period beginning when the fruit is about 1 week before veraison and ending when the fruit is about 3 weeks after the onset of veraison.

In another embodiment, the 3'-methyl-(S)-abscisic acid is applied to *Vitis vinifera* grapes. In a preferred embodiment, the *Vitis vinifera* grapes are selected from the group consisting of Crimson seedless, Flame Seedless, Red Globe, Pinot noir, Cabernet Sauvignon, Syrah, Shiraz, Scarlet Royal, Autumn Royal, and Zinfandel. In a more preferred embodiment, the *Vitis vinifera* grapes are Crimson seedless.

In a further embodiment, the 3'-methyl-(S)-abscisic acid is applied to the plant with another plant growth regulator. In a preferred embodiment, the plant growth regulator is selected from the group consisting of cytokinins, gibberellins, auxins, and ethylene precursors. In a more preferred embodiment, the plant growth regulator is an ethylene precursor. In a preferred embodiment, the ethylene precursor is selected from the group consisting of ethephon or 1-aminocyclopropane carboxylic acid ("ACC"). In a most preferred embodiment, the ethylene precursor is ethephon.

If ethephon is applied with 3'-methyl-(S)-abscisic acid, it may be applied at a rate of from about 50 to 300 grams per acre. In a preferred embodiment, the ethephon may be applied at a rate of from about 100 to 300 grams per acre. In a more preferred embodiment, it may be applied at a rate of from about 150 to 250 grams per acre.

In an alternative preferred embodiment, the abscisic acid derivative applied to the plant is 3'-propargyl-(S)-abscisic acid. In another embodiment, the 3'-propargyl-(S)-abscisic acid is applied to the plant at a rate of from about 0.1 to about 10 mg per cluster. In a preferred embodiment, the 3'-propargyl-(S)-abscisic acid is applied to the plant at a rate of from about 0.2 to about 8 mg per cluster. In a more preferred embodiment, the 3'-propargyl-(S)-abscisic acid is applied to the plant at a rate of from about 0.3 to about 8 mg per cluster.

In a further embodiment, the 3'-propargyl-(S)-abscisic acid is applied to the plant during the period beginning when the fruit is about 3 weeks before veraison and ending when the fruit is about 4 weeks after the onset of veraison. In a preferred embodiment, the 3'-propargyl-(S)-abscisic acid is applied to the plant during the period beginning when the fruit is about 2 weeks before veraison and ending when the fruit is about 4 weeks after the onset of veraison. In a more preferred embodiment, the 3'-propargyl-(S)-abscisic acid is applied to the plant during the period beginning when the fruit is about 1 week before veraison and ending when the fruit is about 4 weeks after the onset of veraison. In a most preferred embodiment, the 3'-propargyl-(S)-abscisic acid is applied to the plant during the period beginning when the fruit is about 1 week before veraison and ending when the fruit is about 3 weeks after the onset of veraison.

In another embodiment, the 3'-propargyl-(S)-abscisic acid is applied to *Vitis vinifera* grapes. In a preferred embodiment, the *Vitis vinifera* grapes are selected from the group consisting of Crimson seedless, Flame Seedless, Red Globe, Pinot noir, Cabernet Sauvignon, Syrah, Shiraz, Scarlet Royal, Autumn Royal, and Zinfandel. In a more preferred embodiment, the *Vitis vinifera* grapes are Crimson seedless.

In a further embodiment, the 3'-propargyl-(S)-abscisic acid is applied with another plant growth regulator to the plant. In a preferred embodiment, the plant growth regulator is selected from the group consisting of cytokinins, gibberellins, auxins, and ethylene precursors. In a more preferred embodiment, the plant growth regulator is an ethylene precursor. In a preferred embodiment, the ethylene precursor is selected from the group consisting of ethephon or ACC. In a most preferred embodiment, the ethylene precursor is ethephon.

If ethephon is applied with 3'-propargyl-(S)-abscisic acid, it may be applied at a rate of from about 50 to 300 grams per acre. In a preferred embodiment, the ethephon may be applied at a rate of from about 100 to 300 grams per acre. In a more preferred embodiment, it may be applied at a rate of from about 150 to 250 grams per acre.

The abscisic acid derivatives claimed herein are enantiomerically pure "(S)" derivatives, meaning that "(2Z, 4E)-5-((S)-1-hydroxy-2,3,6,6-tetramethyl-4-oxocyclohex-2-en-1-yl)-3-methylpenta-2,4-dienoic acid," "(2Z,4E)-5-((S)-1-hydroxy-2,6,6-trimethyl-4-oxo-3-(prop-2-yn-1-yl) cyclohex-2-en-1-yl)-3-methylpenta-2,4-dienoic acid," "3'-propargyl-(S)-abscisic acid," and "3'-methyl-(S)-abscisic acid" refer to derivatives comprising greater than 95% purity of the "(S)" enantiomer. This means that the compounds claimed herein are not "racemic" or "(±)." "Racemic" and "(±)" refer to derivatives with a relatively equal mixture of R/S enantiomers.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases. Suitable salts include inorganic salts such as the ammonium, lithium, sodium, potassium, magnesium and calcium salts and organic amine salts such as the triethylamine, morpholine, triethanolamine, dimethylethanolamine and ethanolamine salts.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1

A field study was conducted in California to compare the efficacy of S-ABA to 3'-methyl-(S)-ABA in promoting red grape coloration. S-ABA and 3'-methyl-(S)-ABA were formulated as aqueous solutions of the corresponding potassium salt to the desired concentrations with the final pHs being between 6.5 and 7.2. Individual Crimson Seedless grape clusters were selected and tagged, with 20 tagged clusters per treatment. The treatments were applied as cluster-directed sprays using a trigger sprayer at 15 to 20 mL per cluster to ensured good coverage of the grapes. Application of 15 to 20 milliliters per cluster simulates application of about 109 gallons per acre directed at the approximately 40 clusters per vine in a vineyard with 518 vines per acre. Based on these estimates, Applicant determined the approximate grams per acre. The equation is as follows: 20 ml/cluster×40 cluster/vine=800 ml/vine×518 vine/acre=(414,400 ml/acre)/(1000 ml/liter)=414 liters/acre. An estimation of grams per acre was made by multiplying the mg per cluster with 20,720 clusters/acre (40 clusters/vine×518 vines/acre=20,720 clusters/acre).

Periodically after the treatments, the grape clusters were evaluated for color development by visual ratings over a six-week period. The coloration was graded on a 1 to 8 grading scale, where a rating of 1 has very little or no red color and a rating of 8 has a deep or dark red color. The percentages of berries that reached marketable red coloration for each cluster were averaged and recorded for each treatment. The data for the percentage of berries with marketable color is shown in Table 1. Additionally, representative berries from each treatment group were harvested about four weeks after treatment and analyzed for anthocyanin content. This data is shown in Table 2.

TABLE 1

Effects of S-ABA and 3'-methyl-(S)-ABA on Grape Coloration

| Treatment | Use Rate | Coloring Ratings, % of the berries with marketable color | | | | |
|---|---|---|---|---|---|---|
| | | 7 DAT | 14 DAT | 27 DAT | 33 DAT | 43 DAT |
| Untreated | n/a | 0 | 8 | 12 | 19 | 26 |
| 3'-methyl-(S)-ABA, K+ salt | 20 ppm, 0.3-0.4 mg/cluster, 6-8 grams/acre | 34 | 67 | 79 | 85 | 89 |
| 3'-methyl-(S)-ABA, K+ salt | 40 ppm, 0.6-0.8 mg/cluster, 12-16 grams/acre | 52 | 83 | 92 | 95 | 97 |
| 3'-methyl-(S)-ABA, K+ salt | 200 ppm, 3-4 mg/cluster, 60-80 grams/acre 200 ppm | 72 | 89 | 95 | 95 | 100 |
| 3'-methyl-(S)-ABA, K+ salt | 400 ppm, 6-8 mg/cluster, 120-160 grams/acre | 76 | 98 | 99 | 99 | 99 |
| S-ABA, K+ salt | 200 ppm, 3-4 mg/cluster, 60-80 grams/acre | 41 | 78 | 84 | 88 | 89 |
| S-ABA, K+ salt | 400 ppm, 6-8 mg/cluster, 120-160 grams/acre | 47 | 80 | 85 | 88 | 91 |

As previously explained, Applicant unexpectedly discovered that a much lower use rate of 3'-methyl-(S)-ABA was required to develop coloration in comparison to S-ABA. Specifically, the data in Table 1 revealed that a treatment with the 40 ppm solution of 3'-methyl-(S)-ABA was even more efficacious than treatment with the same volume of 400 ppm solution of S-ABA treatment, suggesting that 3'-methyl-(S)-ABA was approximately 10 times more active than S-ABA. Further, Applicant unexpectedly discovered that 3'-methyl-(S)-ABA conferred coloration much faster than S-ABA at the same use rate. Thus, at 400 ppm (6 to 8 mg per cluster), 3'-methyl-(S)-ABA gave ~90% marketable coloration in two weeks, whereas it took five or six weeks for S-ABA treated grapes to reach the same level of coloration. Seven days after the other grape clusters were treated, the untreated grapes clusters had no grapes with commercially acceptable color and only 26% of berries reached commercially acceptable levels of redness after six weeks.

TABLE 2

Effects of S-ABA and S-ABA Derivatives on Anthocyanin Content of Grapes

| Treatment | Total Anthocyanin Content, mg/L |
|---|---|
| Untreated | 19 |
| 3'-methyl-(S)-ABA, 0.3-0.4 mg/cluster (20 ppm, 15-20 mL) | 68 |
| 3'-methyl-(S)-ABA, 0.6-0.8 mg/cluster (40 ppm, 15-20 mL) | 78 |
| 3'-methyl-(S)-ABA, 3-4 mg/cluster (200 ppm, 15-20 mL) | 181 |
| 3'-methyl-(S)-ABA, 6-8 mg/cluster (400 ppm, 15-20 mL) | 247 |
| S-ABA, 3-4 mg/cluster (200 ppm, 15-20 mL) | 73 |
| S-ABA, 6-8 mg/cluster (400 ppm, 15-20 mL) | 83 |

Applicant also unexpectedly discovered that the 3'-methyl-(S)-ABA treatments on grapes resulted in higher anthocyanin content than the S-ABA treatments. The results of the anthocyanin analysis shown in Table 2 supports the conclusion that 3'-methyl-(S)-ABA was approximately 10 times more active than S-ABA in promoting Crimson Seedless grape coloration. Thus, grapes treated with 0.3 to 0.4 mg per cluster (20 ppm) and 0.6 to 0.8 mg per cluster (40 ppm) of 3'-methyl-(S)-ABA contained 68 mg per liter and 78 mg per liter of anthocyanin, respectively, compared favorably with the 73 mg per liter and 83 mg per liter of anthocyanin for grapes treated with 3 to 4 mg per cluster (200 ppm) and 6 to 8 mg per cluster (400 ppm), respectively, of S-ABA. The calculated relative potency of 3'-methyl-(S)-ABA was determined to be 8.4 times more potent than S-ABA, meaning that it takes an 8.4 times higher rate of S-ABA to achieve the same effect as 3'-methyl-(S)-ABA.

Example 2

Another trial was conducted in California on Crimson Seedless grapes to compare the efficacy of S-ABA, 3'-methyl-(S)-ABA and 3'-propargyl-(S)-ABA in promoting coloration. All three compounds were formulated as aqueous solutions of the corresponding potassium salt to the desired concentrations, with the final pHs being between 6.5 and 7.2. Individual Crimson Seedless grape clusters were selected and tagged, with 20 tagged clusters per treatment. The solutions were applied as cluster-directed sprays using a trigger sprayer at 15 to 20 milliliters per cluster which ensured good coverage of the grapes. The treatments were applied on day 0 and day 11 of the trial. Periodically during the trial, the grape clusters were evaluated for color development by visual ratings over a six-week period and the coloration was graded on a 1 to 8 grading scale, where a rating of 1 has very little or no red color and a rating of 8 has a deep or dark red color. The data is shown in Table 3.

TABLE 3

Effects of S-ABA and 3'-substituted-(S)-ABA Derivatives on Grape Coloration

| Treatment | Use rate | Color Ratings | | | | | |
|---|---|---|---|---|---|---|---|
| | | 3 DAT | 10 DAT | 14 DAT | 21 DAT | 31 DAT | 41 DAT |
| Untreated | n/a | 1 | 1.2 | 1.3 | 1.6 | 1.6 | 1.6 |
| S-ABA | 3-4 mg/cluster, 60-80 g/acre (200 ppm) | 1 | 2.2 | 2.6 | 4.1 | 5.1 | 5.4 |
| S-ABA | 6-8 mg/cluster, 120-160 g/acre (400 ppm) | 1 | 2.9 | 3.5 | 4.5 | 5.9 | 6.4 |
| 3'-methyl-(S)-ABA, K+ salt | 0.06-0.08 mg/cluster, 1.2-1.6 g/acre (4 ppm) | 1 | 1.6 | 1.9 | 2.4 | 2.7 | 2.8 |
| 3'-methyl-(S)-ABA, K+ salt | 0.3-0.4 mg/cluster, 6-8 g/acre (20 ppm) | 1.3 | 1.7 | 2.3 | 2.9 | 3.5 | 3.5 |
| 3'-methyl-(S)-ABA, K+ salt | 0.6-0.8 mg/cluster, 12-16 g/acre (40 ppm) | 1.1 | 1.3 | 2.7 | 3.9 | 4.7 | 5.5 |
| 3'-propargyl-(S)-ABA, K+ salt | 0.06-0.08 mg/cluster, 1.2-1.6 g/acre (4 ppm) | 1.1 | 1.3 | 1.5 | 1.9 | 2.4 | 2.4 |
| 3'-propargyl-(S)-ABA, K+ salt | 0.3-0.8 mg/cluster, 6-8 g/acre (20 ppm) | 1.1 | 1.5 | 1.8 | 2.2 | 2.9 | 3.1 |
| 3'-propargyl-(S)-ABA, K+ salt | 0.6-0.8 mg/cluster, 12-16 g/acre (40 ppm) | 1.1 | 1.5 | 1.8 | 2.6 | 3.1 | 3.3 |

When the grapes were left untreated, coloration developed very slowly, only achieving a rating of 1.6 at the end of the six-week evaluation period. The grapes treated with S-ABA showed dose-dependent accelerated red color development in comparison with the untreated control, achieving ratings of 5.4 and 6.4 with 3 to 4 mg per cluster (200 ppm solution) and 6 to 8 mg per cluster (400 ppm solution), respectively, at the end of the evaluation period. The grapes treated with 3'-methyl-(S)-ABA also showed dose-dependent accelerated red color development in comparison with the untreated control. Consistent with the results of Example 1, Applicant unexpectedly discovered that 3'-methyl-(S)-ABA was more effective than S-ABA in promoting red color development of Crimson Seedless grapes. Thus, treatment with 0.6 to 0.8 mg per cluster (40 ppm solution) of 3'-methyl-(S)-ABA rendered a coloration rating of 5.5 at the end of the six-week evaluation period, compared to the rating of 5.4 for grapes treated with same volume of 200 ppm of S-ABA.

Treatment with 3'-propargyl-(S)-ABA also accelerated coloration in comparison with the untreated control. Thus, at 0.6 to 0.8 mg per cluster (40 ppm solution) use rate, treatment with 3'-propargyl-(S)-ABA resulted in a color rating of 3.3 at the end of the six-week evaluation period, in comparison with a color rating of 1.6 for untreated control. However, this compound appeared to be less potent than 3'-methyl-(S)-ABA.

The invention claimed is:

1. A method of enhancing red grape coloration comprising applying from about 20 to about 400 parts per million of (2Z,4E)-5-((S)-1-hydroxy-2,3,6,6-tetramethyl-4-oxocyclohex-2-en-1-yl)-3-methylpenta-2,4-dienoic acid (3'-methyl-(S)-abscisic acid) or a salt thereof to the plant.

2. The method of claim 1 wherein the abscisic acid derivative is 3'-methyl-(S)-abscisic acid.

3. The method of claim 2 wherein the 3'-methyl-(S)-abscisic acid is applied at a rate of from about 0.3 to about 8 mg per cluster.

4. The method of claim 3 wherein the 3'-methyl-(S)-abscisic acid is applied at a rate of from about 6 to about 160 grams per acre.

5. The method of claim 2 wherein the 3'-methyl-(S)-abscisic acid is applied to the vine during the period beginning when the fruit is about 3 weeks before veraison and ending when the fruit is about 4 weeks after the onset of veraison.

6. The method of claim 5 wherein the 3'-methyl-(S)-abscisic acid is applied to the vine during the period beginning when the fruit is about 1 week before veraison and ending when the fruit is about 3 weeks after the onset of veraison.

7. The method of claim 2 wherein the 3'-methyl-(S)-abscisic acid is applied to *Vitis vinifera* grapes.

8. The method of claim 2 wherein the 3'-methyl-(S)-abscisic acid is applied with a plant growth regulator selected from the group consisting of cytokinins, gibberellins, auxins, and ethylene precursors.

9. The method of claim 8 wherein the ethylene precursor is ethephon.

* * * * *